United States Patent [19]

Onohara et al.

[11] Patent Number: 4,582,762

[45] Date of Patent: Apr. 15, 1986

[54] SOFT VINYL CHLORIDE RESIN-SILICONE COMPOSITE SHAPED ARTICLE

[75] Inventors: Masayuki Onohara; Masaru Shibata, both of Kanagawa; Akira Igarashi, Yokohama; Nobuhisa Kawaguchi, Kamakura, all of Japan

[73] Assignees: Sumitomo Bakelite Company Ltd.; Fuji Systems Corporation, both of Tokyo, Japan

[21] Appl. No.: 665,978

[22] Filed: Oct. 29, 1984

[30] Foreign Application Priority Data

Nov. 1, 1983 [JP] Japan ............................. 58-203699

[51] Int. Cl.$^4$ .............................................. B32B 9/04
[52] U.S. Cl. ........................... 428/447; 128/DIG. 21; 138/DIG. 7; 428/35; 428/413; 428/451; 428/424.6; 428/518; 428/522; 604/265; 604/266
[58] Field of Search ............... 428/447, 451, 518, 522, 428/35, 448, 424.6; 604/265, 266; 128/DIG. 21; 138/DIG. 7

[56] References Cited

U.S. PATENT DOCUMENTS 4,490,420  12/1984  Yoshida ................................ 428/35

FOREIGN PATENT DOCUMENTS

| 28190 | 8/1971 | Japan . |
| 124953 | 10/1975 | Japan . |
| 127132 | 11/1976 | Japan . |
| 24258 | 2/1977 | Japan . |
| 39751 | 3/1977 | Japan . |
| 125455 | 10/1977 | Japan . |
| 61242 | 5/1979 | Japan . |
| 101884 | 8/1979 | Japan . |
| 81362 | 7/1981 | Japan . |

*Primary Examiner*—Edith Buffalow
*Attorney, Agent, or Firm*—Karl W. Flocks; Sheridan Neimark

[57] ABSTRACT

A soft vinyl chloride resin-silicone composite shaped article consisting of a soft vinyl chloride resin shaped article and a cured layer of an addition polymerization type silicone composition adhered to the surface of the vinyl chloride resin shaped article, wherein said addition polymerization type silicone composition contains an organohydrogenpolysiloxane having at least two hydrogen atoms directly bonding with silicon atoms in each molecule, in an amount enough to provide one to six such hydrogen atoms per one vinyl group of the silicone composition. The above composite shaped article has a very high bonding strength between the vinyl chloride resin shaped article and the cured layer of an addition polymerization type silicone composition.

3 Claims, No Drawings

SOFT VINYL CHLORIDE RESIN-SILICONE COMPOSITE SHAPED ARTICLE

BACKGROUND OF THE INVENTION

1. Field of the Invention

This invention relates to a vinyl chloride resin-silicone composite shaped article.

2. Description of the Prior Art

Vinyl chloride resins can have flexibility by the addition of a plasticizer, a high molecular elastomer or the like, excel in transparency and are good in adhesion and processability by high frequency or other method. Hence, they have been widely used in medical utensils, food packaging, etc. However, when used in the field of medical utensils, vinyl chloride resin products are inferior in thrombus resistance and histocompatibility; therefore, these products cause various inconveniences in applications where the products come in direct contact with blood or in applications where the products are used in human bodies for a long period of time.

On the other hand, silicones have been excepted, as a medical material for their superiority in thrombus resistance and histocompatibility. However, they are used only in a limited amount in medical field because of their high cost and low mechanical strength.

With a view to utilizing the strength of a vinyl chloride resin and a silicone and to making up for each other's weaknesses, there were made many attempts of using a vinyl chloride resin and a silicone as a composite material by incorporating the latter into the former or coating the latter on the former. However, it has been generally thought that strong adhesion between a soft vinyl chloride resin and a silicone is difficult due to the effect of additives contained in the vinyl chloride resin such as a plasticizer and the like. In order to overcome this drawback, there were proposed various methods in which the surface of a soft vinyl chloride resin is treated, for example, with a primer and then a silicone layer is formed thereon. However, these methods had drawbacks in that (a) the process is complex, (b) many primers use a solvent such as ethyl acetate, toluene or the like and the solvent may remain partly and (c) the adhesion between the vinyl chloride resin and the silicone layer causes separation with the layer of time.

Japanese Laid-open Patent Application No. 156083/79 proposed a method wherein the surface of a vinyl chloride resin is subjected to plasma treatment at low temperatures and then thereon is formed a cured layer of an RTV silicone rubber of condensation polymerization type. Japanese Patent Application Kokai (Laid-Open) No. 32773/83 proposed the modification of a vinyl chloride resin material in which the surface of the vinyl chloride resin material is subjected to room temperature plasma treatment or the like to form a cured layer and then thereon is formed a silicone resin layer composed of a dimethylpolysiloxane or an alkyl group-modified dimethylpolysiloxane. From these methods, it is clear that a silicone resin can be allowed to adhere to the surface of a vinyl chloride resin. However, it is difficult to subject the inner surface of a small diameter tube or a long tube made of a vinyl chloride resin to complete room temperature plasma treatment to form a cured layer.

SUMMARY OF THE INVENTION

With a view to realizing direct and strong adhesion of a silicone layer of high thrombus resistance to the surface of a soft vinyl chloride resin shaped article which had been thought to be difficult, without forming beforehand a cured layer on the surface of the soft vinyl chloride resin shaped article by plasma treatment or the like or without applying to the surface a pretreatment such as primer treatment or the like, the present inventors made an extensive study on silicones and vinyl chloride resins. As a result, it has been found that surprisingly there is a combination of a soft vinyl chloride resin and a silicone wherein they can adhere to each other.

According to the present invention, there is provided a soft vinyl chloride resin-silicone composite shaped article consisting of a soft vinyl chloride resin shaped article and a cured layer of an addition polymerization type silicone composition adhered to the surface of the vinyl chloride resin shaped article, wherein said addition polymerization type silicone composition contains an organohydrogenpolysiloxane having at least two hydrogen atoms directly bonded to silicone atoms in each molecule, in an amount enough to provide one to six such hydrogen atoms per one vinyl group of the silicone composition.

DETAILED DESCRIPTION OF THE INVENTION

The addition polymerization type silicone in the present invention is a composition consisting of (a) a polysiloxane containing vinyl groups represented by the formula (1)

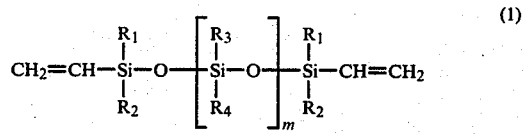

wherein $R_1$, $R_2$, $R_3$ and $R_4$ may be same or different and are each a monovalent hydrocarbon group having 6 or less carbon atoms and m is a positive integer, (b) an organohydrogenpolysiloxane represented by the formula (2)

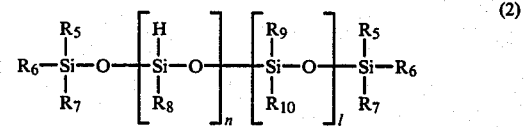

wherein $R_5$, $R_7$, $R_8$, $R_9$ and $R_{10}$ may be same or different and are each a monovalent hydrocarbon group having 6 or less carbon atoms, two $R_6$'s are hydrogen atoms or the same or different monovalent hydrocarbon groups having 3 or less carbon atoms, n is an integer of 2 to 100 and l is an integer of 0 to 100 and (c) an inorganic substance as a reinforcing component such as silica or the like. The composition can be converted into a solid elastomer when subjected to addition polymerization in the presence of a platinum type catalyst.

The present inventors found that an addition polymerization type silicone composition can have a very high bonding strength toward a soft vinyl chloride resin if the silicone composition contains an organohydrogenpolysiloxane represented by the formula (2) having at least two hydrogen atoms directly bonded to silicone atoms in each molecule, in an amount enough to provide one to six such hydrogen atoms per one vinyl group in the formula (1).

A similarly high bonding strength can be obtained even if the above addition polymerization type silicone composition containing the above organohydrogenpolysiloxane in said amount further contains, as adhesion improvers, at least one compound selected from epoxy compounds, carboxylic acid anhydrides, silanes or siloxanes having an acryloxyalkyl group represented by the general formula (3), $$CH_2=C-C-(CH_2)_n-Si\equiv \qquad (3)$$
$$\phantom{CH_2=C}|\phantom{C}\|$$
$$\phantom{CH_2=C}R\phantom{C}O$$

wherein R is $CH_3$ or a hydrogen atom and n is an integer of 1 to 3, and unsaturated hydrocarbon group-containing oxysilane compounds which are all used in so-called self-adhesing silicone rubbers.

The presence of these adhesion improvers further enhances the bonding strength of the addition polymerization type silicone composition. Accordingly, in adhesion between a soft vinyl chloride resin and an addition polymerization type silicone composition, it is essential that the silicone composition contains an organohydrogensiloxane having at least two hydrogen atoms directly bonded to silicone atoms in each molecule, in an amount enough to provide such hydrogen atoms in such an excess that the physical properties of the silicone composition after curing is not greatly impaired, relative to total vinyl groups present in the silicone composition. Further, it was found that addition of an ordinarily known adhesion improver brings about a synergistic effect in bonding strength.

The strength of the cured layer of the addition polymerization type silicone composition of the present invention can be enhanced by incorporating into the composition a resinous copolymer containing vinyl groups which is compatible with components of the formulas (1) and (2). As one example of such a copolymer, there is an organopolysiloxane obtained from copolymerization of the following formulas (4), (5) and (6):

$$(CH_2=CH)(R_{11})(R_{12})SiO_{0.5} \qquad (4)$$

$$SiO_2 \qquad (5)$$

$$(R_{13})_3SiO_{0.5} \qquad (6)$$

In the above formulas, $R_{11}$, $R_{12}$ and $R_{13}$ may be same or different and are each a monovalent hydrocarbon group having 6 or less carbon atoms.

As described in Japanese Patent Publication Nos. 45098/80 and 33256/78 and other literature references, it is a known fact that compositions between an addition polymerization type silicone and other components adhere strongly to metals, ceramics, etc. However, there has hitherto been no reporting that these addition polymerization type silicone compositions adhere strongly to soft vinyl chloride resins. Rather, adhesion between a silicone and a soft vinyl chloride resin has been thought to be extremely difficult.

The soft vinyl chloride resin of the present invention is a composition comprising (1) a main component of a vinyl homopolymer or a copolymer composed essentially of vinyl chloride such as a vinyl chloride-ethylene copolymer, a vinyl chloride-vinyl acetate copolymer, a vinyl chloride-ethylene-vinyl acetate terpolymer, a vinyl chloride-acryl copolymer, vinyl chloride-urethane copolymer or the like, and (2) a plasticizer which imparts flexibility to the main component. As the plasticizer, there can be used, for example, fatty acid esters such as phthalic acid esters (e.g. dioctyl phthalate), aliphatic dibasic acid esters (e.g. dioctyl adipate, dibutyl sebacate) and the like, polyester type plasticizers, epoxidized soybean oil, epoxidized linseed oil, etc. Use of these plasticizers in a large amount tends to reduce the adhesion strength of the soft vinyl chloride resin to an addition polymerization type silicone composition. Of these plasticizers, phthalic acid esters such as dioctyl phthalate, epoxidized soybean oil and epoxidized linseed oil can retain the adhesion strength of the soft vinyl chloride resin fairly well and therefore they are particularly preferred plasticizers. Besides, non-liquid high molecular substances capable of imparting flexibility to vinyl chloride resins, such as urethane polymer, EVA and the like can also be used as plasticizers.

Further, as a stabilizer for imparting heat resistance and heat stability, there can be used in the soft vinyl chloride resin of the present invention (1) metal soaps such as Ca stearate, Zn stearate, Mg stearate, Pb stearate and the like, (2) organometal and inorganic metal stabilizers of the above metals, (3) organotin type stabilizers, (4) organic silicone type stabilizers, and (5) ester type stabilizers such as butyl stearate. Of these, there are preferred metal soaps such as Ca stearate, Zn stearate, Pb stearate, Ba stearate and the like as well as organometal and inorganic metal stabilizers of the above metals. Organotin type stabilizers are effective only when a plasticizer is used in a small amount, and they may reduce the adhesion strength between the vinyl chloride resin and the addition polymerization type silicone composition when the plasticizer is contained in 50 parts or more. Ester type stabilizers (e.g. butyl stearate) and phosphoric acid type stabilizers greatly impair curing of the silicone composition when they are used in combination, therefore, these two types of stabilizers can not be used in combination.

In the vinyl chloride resin, there can also be used additives such as an ultraviolet inhibitor, a pigment, an antistatic agent, an X-ray contrast medium and the like. As a lubricant for imparting lubricity, there can be used higher fatty acids, higher alcohols, low molecular polyethylenes, amides, esters and the like. Higher fatty acids as external lubricant, such as stearic acid and the like tends to plate out on the surface of the vinyl chloride resin, therefore, their amounts must be restricted. External lubricants such as stearic acid and the like are used preferably in an amount of 0.5 part or less, particularly when they are used in combination with barium sulfate employed in medical field as an X-ray contrast medium, bismuth subcarbonate, etc.

As described above, widely known components are used in the soft vinyl chloride resin of the present invention. The mechanism of adhesion by curing between the soft vinyl chloride resin and the addition polymerization type silicone composition of the present invention has not yet been thoroughly clarified. As one possible reason for this adhesion, there is surmised an addition reaction between vinyl groups of the vinyl chloride resin and hydrogen atoms directly bonded to silicon atoms, of the silicone composition. Hitherto it has been well known that components having hydrogen atoms directly bonding with silicon atoms cause an addition reaction with olefins in the presence of a catalyst such as chloroplatinic acid, a chloroplatinic acid-olefin complex, platinum-carbon, potassium chloroplatinoate-olefin, a metal carbonyl and the like. This reaction is expressed by the following general formula (9):

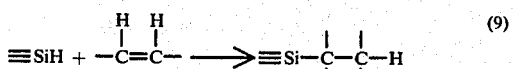

However, with respect to soft vinyl chloride resins containing liquids such as a plasticizer and the like in a large amount, there has been issued no study paper regarding their adhesion with compounds having hydrogen atoms directly bonded to silicon atoms. It has been thought that the presence of a plasticizer in soft vinyl chloride resins impairs their adhesion with addition polymerization type silicone compositions.

The present invention is based on a finding of a possibility of an addition reaction between double bonds of vinyl groups or active carbons in a vinyl chloride resin and hydrogen atoms directly bonded to silicon atoms in an addition polymerization type silicone composition. That is, since it is essential that an organohydrogen siloxane is contained in excess in the silicone composition, it is indispensable in this case that free vinyl groups remain in the soft vinyl chloride resin, and in particular, the free vinyl groups are formed during the processing. This can be understood from the fact that the adhesion strength between the vinyl chloride resin and the addition polymerization type silicone composition increases as the amount of a stabilizer in the vinyl chloride resin decreases.

The soft vinyl chloride resin-silicone composite shaped article according to the present invention can be produced, desirably by the following process. That is, on the surface of a soft vinyl chloride resin shaped article, there is laminated an addition polymerization type silicone composition or a solution of the composition dissolved in an organic solvent, by a method such as coating, dipping, spraying or the like. (In this case, a pretreatment such as primer treatment is not required at all for the above surface.) Then, this integral body is subjected to heat treatment at 40° to 130° C., preferably 80° to 120° C. for 5 min to 10 hr, preferably 10 min to 3 hr, whereby a cured layer is formed on the soft vinyl chloride resin shaped article. Certain kinds of addition polymerization type silicone compositions using a chloroplatinic acid catalyst can cure in a period of time as short as 30 sec at 100° C. to form a desired film, however, in such a short time, no sufficient adhesion strength can be obtained with vinyl chloride resins. Certain other kinds of addition polymerization type silicone compositions containing a platinum type catalyst can cure in 5 min to 3 days at 30° C., however, no sufficient adhesion strength can be obtained as well. Reasons for these poor bonding strengths will be, for example, that, in these kinds of addition polymerization type silicone compositions, the reaction between their hydrogen atoms directly bonded to silicon atoms and vinyl groups in the vinyl chloride resin is slow, or, heat treatment for curing induces thermal decomposition of the vinyl chloride resin resulting in formation of carbon to carbon double bonds.

The cured layer of the addition polymerization type silicone composition thus formed adheres very strongly to the surface of the soft vinyl chloride resin shaped article. This adhesion does not deteriorate with the lapse of time and also even after a severe treatment such as autoclave or the like. The composite shaped article of the present invention excels in thrombus resistance, is free from staying thereon of acetic acid, alcohols, oximes and the like as experienced particularly in RTV silicone rubbers of condensation polymerization type, and accordingly can be suitably used in medical devices particularly in circuits directly contacting with blood, catheters, drains, and other devices of long term usage.

DESCRIPTION OF THE PREFERRED EMBODIMENTS

EXAMPLE 1

Soft vinyl chloride resin compositions shown in Table 1 were kneaded at 160° C. for 5 min by a roll and then subjected to press molding at 200° C. for 4 min, whereby respective sheets of 0.5 mm thickness were prepared. These sheets were cut into pieces each of 20 mm×50 mm. Each two pieces of the same kind were laminated with a silicone placed between them in an amount of 0.5 g per unit area of 20 mm×20 mm. Each laminate was heated at 110° C. for 1 hr and then allowed to stand for curing, whereby each test piece was prepared. These test pieces were subjected to tests to evaluate their performances. The results are shown in Table 1. In Table 1, bonding strength was measured in 180° peel by the use of a universal tensile testing instruments, and the autoclave conditions were 120° C. and 1 hr.

TABLE 1

| Formulation of vinyl chloride resin composition (phr) | Vinyl chloride resin | | | 100 | | | | 100 | | |
|---|---|---|---|---|---|---|---|---|---|---|
| | Dioctyl phthalate | | | 100 | | | | 50 | | |
| | Metal (Ca—Zn) weight in stabilizer | | | 0.05 | | | | 0.05 | | |
| | Epoxidized soybean oil | | | 10 | | | | 10 | | |
| Kind of silicone *2 | | A | B | C | D | E | A | B | C | D | E |
| Result | Bonding strength (kg/20 mm width) | 0 | 3.2 | 5.3 | 0 | 0.1 | 0 | 5.6 | 8.0 | 0.1 | 0.15 |
| | Bonding strength after autoclave treatment | 0 | 3.0 | 5.0 | 0 | 0 | 0 | 4.5 | 7.1 | 0 | 0 |
| | Change of bonding strength with time (kg/20 mm width) | 0 | 3.1 | 4.9 | 0 | 0 | 0 | 5.4 | 7.4 | 0 | 0 |

*1 SX-DH, manufactured by SUMITOMO CHEMICAL CO., LTD.
*2 Details of A, B, C, D and E are shown in pages which follow. A, B and C are addition polymerization type silicones. D and E are condensation type silicones.

Silicone A

This silicone was prepared by adding, to (a) 100 parts of a dimethylpolysiloxane having dimethylvinylsilyl groups at both ends of the molecular chain and having a viscosity of 12,000 cs at 25° C., (b) 4 parts of a polysiloxane whose methylhydrogenpolysiloxane component consists of 12 mole % of trimethylsiloxane unit, 48 mole % of dimethylsiloxane and 40 mole % of methylhydrogensiloxane, (c) 30 parts of silica and (d) 0.1 part of an isopropyl alcohol solution of chloroplatinic acid (5% of platinum in the solution).

Silicone B

This silicone was prepared by adding to, (a) 100 parts of a dimethylpolysiloxane having dimethylvinylsilyl groups at both ends of the molecular chain and having a viscosity of 18,000 cs at 25° C., (b) 5 parts of a polysiloxane consisting of 10 mole % of trimethylsiloxane unit, 40 mole % of dimethylsiloxane unit and 50 mole % of methylhydrogensiloxane unit, (c) 20 parts of silica and (d) 0.2 part of an isopropyl alcohol solution of chloroplatinic acid (1% of platinum in the solution).

Silicone C

This silicone was prepared by adding, to (a) 100 parts of a dimethylpolysiloxane having dimethylvinylsilyl groups at both ends of the molecular chain and having a 1,300 cs at 25° C., (b) 15 parts of a conventionally known copolymer consisting of $(CH_3)_3SiO_{0.5}$ unit, $(CH_2\!=\!CH)(CH_3)_2SiO_{0.5}$ unit and $SiO_2$ unit wherein the ratio of (1) the sum of the number of $(CH_3)_3SiO_{0.5}$ unit and the number of $(CH_2\!=\!CH)(CH_3)_2SiO_{0.5}$ unit and (2) the number of $SiO_2$ unit is 0.8:1 and the content of vinyl group is 0.9% by weight, (c) 25 parts of trimethylsilyl-treated silica in the form of aerosol, (d) 5 parts of a methylhydrogenpolysiloxane containing about 50 mole % of methylhydrogensiloxane unit and having a viscosity of 50 cs at 25° C., (e) 0.2 parts of an isopropyl alcohol solution of chloroplatinic acid (1% of platinum in the solution), (f) 2 parts of an epoxy compound having the following structural formula,

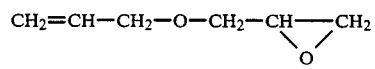

and (g) 0.5 parts of phthalic anhydride.

Silicone D

A condensation type silicone, namely, KE-42-RTV manufactured by Shin-Etsu Chemical Co., Ltd.

Silicone E

A condensation type silicone, namely, KE-45-RTV manufactured by Shin-Etsu Chemical Co., Ltd.

As is obvious from Table 1, the soft vinyl chloride resin-silicone composite sheet prepared in Example 1 had high bonding strengths and the strengths showed only minor changes after an autoclave treatment or with the lapse of time.

EXAMPLE 2

Various soft vinyl chloride resin compositions shown in Table 2 were extruded into respective sheets each of 0.8 mm thickness at 170° to 190° C. by the use of a 40 mm extruder. In the same manner as in Example 1, the adhesivities of these sheets with silicone C were evaluated. The results are shown in Table 2.

As is obvious from Table 2, bonding strength between a soft vinyl chloride resin composition and a silicone was poor when an organotin type stabilizer or a phosphorus type stabilizer was used in the vinyl chloride composition. Also, use of an excessive amount of stearic acid as an external lubricant in the resin composition impaired the adhesion strength between the vinyl chloride resin composition and a silicone.

TABLE 2

| | Silicone | | | | | | | B |
|---|---|---|---|---|---|---|---|---|
| Formulation of vinyl chloride composition (phr) | Vinyl chloride resin | | | | 100 | | | |
| | Dioctyl phthalate | | | | 50 | | | |
| | Epoxidized soybean oil | | | | 10 | | | |
| | Stabilizer | Ca stearate 0.5 | Zn stearate 0.5 | Ca—Zn stabilizer 1.0  3.0 | Organotin type stabilizer 0.2  1.0 | Phosphorus type stabilizer 0.5 Butyl stearate 0.5 | Ca—Zn stabilizer 3.0 | |
| | Lubricant | 0 | 0 | 0  0 | 0  0 | 0 | Stearic acid 2.0 | |
| Result | Bonding strength (kg/20 mm width) | 6.4 | 7.6 | 7.8  4.5 | 2.1  0 | 0 | 0 | |

EXAMPLE 3

A resin composition consisting of 100 parts by weight of a vinyl chloride resin (S-101 manufactured by SUMITOMO CHEMICAL CO., LTD.), 65 parts by weight of a dioctyl phthalate, 0.05 part by weight (as metal) of Ca stearate and Zn stearate and 7 parts by weight of an epoxidized soybean oil was extruded into films of 0.1 mm thickness. Various silicones diluted with n-hexane were coated on these films so that each coating after curing had a thickness of about 60μ. The solvent in the coating was evaporated at room temperature and then each coated film was cured at 100° C. for 2 hr, whereby test films were prepared. These test films were used in a test for blood coagulability by the Imai-Nose method. Using each test film, a lower film was cut into a size of 30 mm × 30 mm and an upper film was cut into a size of 15 mm × 15 mm. On the lower film there was dropped 0.25 ml of a dog's fresh blood just after drawing to which ACD had been added. To the blood was added 0.025 ml of a 3.8% aqueous calcium chloride solution and they were mixed thoroughly. Then, the upper film was placed thereon. In this case, the two films were arranged so that their silicone sides came in contact with the blood. Each set consisting of a lower film, the blood and an upper film was allowed to stand in an atmosphere of saturated water vapor of 37° C. After 5 min, 10 min and 20 min incubation, the uncoagulated portion of the blood was washed away each time by the use of 50 cc of distilled water. Then, only blood clot was fixed by 37% formalin and, after washing and drying, the blood clot was weighed. The results are shown in Table 3.

TABLE 3

| Film | Weight of blood clot (mg) | | | Remarks |
|---|---|---|---|---|
| | After 5 min | After 10 min | After 20 min | |
| Vinyl chloride resin only | 8 | 15 | 21 | |
| Vinyl chloride resin coated with an addition type silicone *1 | Trace | 5 | 12 | Bonding strength was high. |
| Vinyl chloride resin coated with a condensation polymerization type silicone *2 | 5 | 22 | 29 | The silicone peeled during dipping in distilled water. |

*1 This silicone was prepared by adding, to 100 parts of a dimethylpolysiloxane having dimethylvinylsilyl group at both ends of the molecular chain and having a viscosity of 5,000 cs at 25° C., 12 parts of a polysiloxane consisting of 8 mole % of trimethylsiloxane unit, 50 mole % of dimethylsiloxane unit and 42 mole % of methylhydrogensiloxane unit, 35 parts of silica, 2 parts of an epoxy compound represented by the following formula, $$CH_3O-\underset{\underset{OCH_3}{|}}{\overset{\overset{OCH_3}{|}}{Si}}-CH_2-CH_2-\text{(cyclohexyl-epoxide)}$$

and 1 part of a carboxylic acid anhydride represented by the following formula, $$\text{(benzophenone tetracarboxylic dianhydride structure)}$$

*2 KE-45-RTV, manufactured by Shin-Etsu Chemical Co., Ltd.

As is obvious from Table 3, the soft vinyl chloride resin-silicone composite film had a high adhesion strength and exhibited an excellent thrombus resistance.

What is claimed is:

1. A soft vinyl chloride resin-silicone composite shaped article consisting of a soft vinyl chloride resin shaped article and a cured layer of an addition polymerization type silicone composition adhered to the surface of the vinyl chloride resin shaped article, wherein said addition polymerization type silicone composition contains an organohydrogenpolysiloxane having at least two hydrogen atoms directly bonded to silicon atoms in each molecule, in an amount enough to provide one to six such hydrogen atoms per one vinyl group of the silicone composition.

2. A soft vinyl chloride resin-silicone composite shaped article according to claim 1, wherein the addition polymerization type silicone composition further contains, as components for improving its bonding strength, at least one compound selected from the group consisting of epoxy compounds, carboxylic acid anhydrides, silanes or siloxanes having an acryloxyalkyl group represented by the formula, $$CH_2=\underset{R}{\overset{}{C}}-\underset{O}{\overset{\|}{C}}-(CH_2)_n-Si\equiv$$

wherein R is $CH_3$ or a hydrogen atom and n is an integer of 1 to 3, and unsaturated hydrocarbon group-containing oxysilane compounds.

3. A soft vinyl chloride resin-silicone composite shaped article according to claim 1, wherein the soft vinyl chloride resin contains a stabilizer and the stabilizer contains at least one metal selected from the group consisting of Ca, Zn, Ba, Mg and Al.

* * * * *

UNITED STATES PATENT AND TRADEMARK OFFICE
CERTIFICATE OF CORRECTION

PATENT NO. : 4,582,762
DATED : April 15, 1986
INVENTOR(S) : Onohara et al

It is certified that error appears in the above-identified patent and that said Letters Patent is hereby corrected as shown below:

Column 3, line 9, "acryloxyalkyl" should read --acryloylalkyl--
Column 10, line 44, "acryloxyalkyl" should read --acryloylalkyl--

Signed and Sealed this

Sixth Day of January, 1987

Attest:

DONALD J. QUIGG

Attesting Officer

Commissioner of Patents and Trademarks